United States Patent
Stimpson et al.

(10) Patent No.: US 9,281,219 B2
(45) Date of Patent: Mar. 8, 2016

(54) MOLECULAR RECEPTOR-BASED CHEMICAL FIELD-EFFECT TRANSISTOR (CHEMFET) DEVICES, SYSTEMS, AND METHODS FOR IN-SITU NITRATE MONITORING IN FIELD SOILS

(71) Applicant: SUPRASENSOR TECHNOLOGIES, LLC, Eugene, OR (US)

(72) Inventors: Calden Carroll Stimpson, Eugene, OR (US); Jordan Richard Kusiek, Eugene, OR (US)

(73) Assignee: SUPRASENSOR TECHNOLOGIES, LLC, Eugene, OR (US)

( * ) Notice: Subject to any disclaimer, the term of this patent is extended or adjusted under 35 U.S.C. 154(b) by 0 days.

(21) Appl. No.: 14/489,195

(22) Filed: Sep. 17, 2014

(65) Prior Publication Data

US 2015/0076567 A1    Mar. 19, 2015

Related U.S. Application Data

(60) Provisional application No. 61/879,580, filed on Sep. 18, 2013.

(51) Int. Cl.
*G01N 27/403* (2006.01)
*H01L 21/56* (2006.01)
(Continued)

(52) U.S. Cl.
CPC .............. *H01L 21/56* (2013.01); *G01N 27/414* (2013.01); *H01L 21/565* (2013.01); *H01L 23/3121* (2013.01); *H01L 2924/0002* (2013.01)

(58) Field of Classification Search
CPC .... G01N 27/414; H01L 21/56; H01L 21/565; H01L 23/3121

USPC ............................................ 257/253; 438/49
See application file for complete search history.

(56) References Cited

U.S. PATENT DOCUMENTS 4,059,499 A    11/1977    Nielsen et al.
4,273,636 A     6/1981    Shimada et al.
(Continued)

FOREIGN PATENT DOCUMENTS

EP    0455705 B1    5/1997
EP    1287345 A2    3/2003
(Continued)

OTHER PUBLICATIONS

PCT/US14/56144, Written Opinion of the International Searching Authority, Feb. 25, 2015.
(Continued)

*Primary Examiner* — Trung Q Dang
(74) *Attorney, Agent, or Firm* — David A. Crowther

(57) ABSTRACT

Embodiments include a method for securing a membrane material to a gate of a molecular receptor-based chemical field-effect transistor (CHEMFET). The method can include casting a membrane material onto an exposed region of the gate, curing the membrane material, placing the CHEMFET into a mold, inserting a single application of impervious electrically insulative resin into the mold, and securing edges of the membrane material by the single application of the impervious electrically insulative resin, thereby physically preventing lifting off of the membrane material from the gate. Embodiments include a sensor module. The sensor module can include a CHEMFET, an amplifier circuit, one or more sensor pins for contacting field ground soil, a data logger, and a wireless transceiver, among other components.

20 Claims, 13 Drawing Sheets

(51) Int. Cl.
*G01N 27/414* (2006.01)
*H01L 23/31* (2006.01)

(56) References Cited

U.S. PATENT DOCUMENTS

| | | | |
|---|---|---|---|
| 4,322,680 A * | 3/1982 | Janata | G01N 27/414 324/71.2 |
| 4,502,938 A * | 3/1985 | Covington | A61B 5/14542 204/403.06 |
| 4,701,253 A | 10/1987 | Ligtenberg et al. | |
| 4,772,377 A | 9/1988 | Geist et al. | |
| 5,240,573 A | 8/1993 | Carey | |
| 5,911,873 A | 6/1999 | McCarron et al. | |
| 7,160,690 B2 | 1/2007 | Orser et al. | |
| 7,803,946 B2 | 9/2010 | Haley et al. | |
| 7,927,883 B2 | 4/2011 | Tuli et al. | |
| 8,340,828 B2 | 12/2012 | Danieli | |
| 8,702,964 B2 | 4/2014 | Ahmad | |
| 2006/0148118 A1 * | 7/2006 | Hsiung | G01N 27/4148 438/49 |
| 2007/0096066 A1 | 5/2007 | Yoshida et al. | |
| 2010/0283993 A1 | 11/2010 | Preiner et al. | |
| 2011/0299085 A1 | 12/2011 | Preiner et al. | |
| 2012/0002192 A1 | 1/2012 | Preiner et al. | |
| 2012/0103077 A1 | 5/2012 | Koshnick et al. | |
| 2012/0147368 A1 | 6/2012 | Preiner et al. | |
| 2013/0019664 A1 | 1/2013 | Preiner et al. | |
| 2013/0073097 A1 | 3/2013 | Vidovich | |

FOREIGN PATENT DOCUMENTS

| | | |
|---|---|---|
| EP | 1565736 B1 | 1/2007 |
| WO | 9201219 A1 | 1/1992 |
| WO | 2004048960 A1 | 6/2004 |
| WO | 2009066981 A1 | 5/2009 |
| WO | 2009157755 A2 | 12/2009 |
| WO | 2010114580 A1 | 10/2010 |
| WO | 2010129874 A1 | 11/2010 |
| WO | 2011034413 A1 | 3/2011 |

OTHER PUBLICATIONS

Adamchuck, Viacheslave I. et al., Feasibility of On-the-go Mapping of Soil Nitrate and Potassium Using Ion-Selective Electrodes, Jul. 28, 2002, ASAE, Paper No. 02-1183.

Antonisse, Martijn M.G. et al., Durable nitrate-selective chemically modified field effect transistors based on new polysiloxane membranes, Mar. 16, 1996, Analytica Chimica Acta 332 (1996) 123-129.

Artigas, J. et al., Application of ion sensitive field effect transistor based sensors to soil analysis, Elsevier, Computers and Electronics in Agriculture 31 (2001) 281-293.

Gieling, Th.H et al., ISE and Chemfet sensors in greenhouse cultivation, Elsevier, Dec. 9, 2004.

Sibley, Kevin J. et al., In-field measurement of soil nitrate using an ion-selective electrode, Advances in Measurement Systems, Apr. 1, 2010, Milind KrSharma (Ed.), ISBN: 978-953-307-061-2.

Stauthamer, W.P.R.V. et al., Influence of plasticizer on the selectivity of nitrate-sensitive CHEMFETs, Mar. 18, 1993, Sensor and Actuators B, 17 (1994) 197-201.

Sudholter, Ernst J.R. et al., Modification of ISFETs by covalent anchoring of poly(hydroxyethyl methacrylate) hydrogel. Introduction of a thermodynamically defined semiconductor-sensing membrane interface, Jul. 7, 1989, Laboratory of Organic Chemistry, University of Twente.

Sutton, P.G. et al., Development of a sensitive nitrate-selective electrode for on-site use in fresh waters, Feb. 15, 1999, Department of Environmental Sciences, University of Plymouth.

* cited by examiner

MOLECULAR RECEPTOR-BASED CHEMICAL FIELD-EFFECT TRANSISTOR (CHEMFET) DEVICES, SYSTEMS, AND METHODS FOR IN-SITU NITRATE MONITORING IN FIELD SOILS

RELATED APPLICATION DATA

This application claims the benefit of provisional Application Ser. No. 61/879,580, filed Sep. 18, 2013, which is hereby incorporated by reference.

GOVERNMENT CONTRACT

This invention was made with government support under NSF-IIP-1248984 and NSF-IIP-1341564 awarded by the National Science Foundation. The government has certain rights in the invention.

FIELD OF THE INVENTION

This application pertains to in-situ nitrate monitoring in field soils, and more particularly, to molecular receptor-based chemical field-effect transistor (CHEMFET) devices and methods for in-situ nitrate monitoring in field soils.

BACKGROUND

Of the total nitrate fertilizer used in the US, approximately 30% is lost due to over-application and subsequent seepage into groundwater, volatilization or tiling and runoff. Novel techniques in irrigation and soil moisture monitoring have provided growers the necessary data to manage irrigation, allowing for better forecasting and immediate feedback resulting in decreased water costs and optimized management practices.

However, a general lack of development in new technology for detailed management of soil nutrient levels has disallowed this same type of precision in fertilization. Currently, soil nutrients are monitored prior to and several times during the growing season by collecting 15-20 soil samples from across each 5-20 acre field and mailing these samples to off-site laboratories for analysis. Typically, nutrient testing is performed several times per growing season, resulting in addressable costs over $3 billion. Even with such a staggering cost figure, the investment does not always correlate to optimal crop yields. The lack of correlation is due to the inherent disconnect between the time the sample is taken and the results returned, during which time nitrate levels are affected by the action on ammonium of endogenous soil bacteria, seepage below the root zone with over-watering or over application of fertilizers, or degradation/volatilization during the drying process.

Efforts to improve the lag time between sample collection and actionable data have been made, but the process still typically requires between 3-5 business days, up to the best cases still requiring hours between sampling and results. All current direct methods of nitrate monitoring require pre-processing of the sample, and the nitrate is measured in the filtrate. This is due to the need for a good soil contact, which is typically lacking in standard ion-selective electrodes (ISEs).

Accordingly, a need remains for improved devices, systems, and methods for incorporation of a molecular receptor with a known affinity and selectivity for nitrate, providing a driving force for partitioning nitrate into the membrane, and allowing for direct measurement in soils of varying moisture. Additionally, there is a need for increased accuracy due to the selectivity of the receptor over typical non-specific ISE membranes. Embodiments of the invention address these and other limitations in the prior art.

The foregoing and other features of the invention will become more readily apparent from the following detailed description, which proceeds with reference to the accompanying drawings.

DETAILED DESCRIPTION OF THE EMBODIMENTS

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details. In other instances, well-known methods, procedures, components, circuits, and networks have not been described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first sensor could be termed a second sensor, and, similarly, a second sensor could be termed a first sensor, without departing from the scope of the inventive concept.

It will be understood that when an element or layer is referred to as being "on," "coupled to" or "connected to" another element or layer, it can be directly on, directly coupled to or directly connected to the other element or layer, or intervening elements or layers may be present. In contrast, when an element is referred to as being "directly on," "directly coupled to" or "directly connected to" another element or layer, there are no intervening elements or layers present. Like numbers refer to like elements throughout. As used herein, the term "and/or" includes any and all combinations of one or more of the associated listed items.

The terminology used in the description of the inventive concept herein is for the purpose of describing particular embodiments only and is not intended to be limiting of the inventive concept. As used in the description of the inventive concept and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1A:
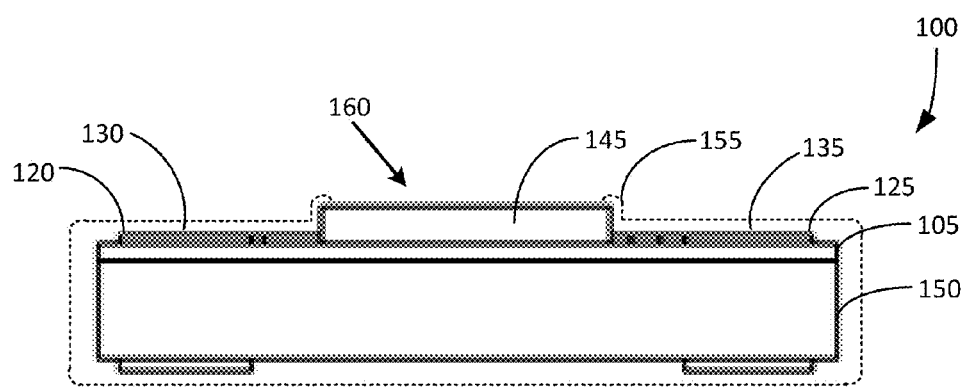
FIG. 1A illustrates a side elevation view of a molecular receptor-based CHEMFET in accordance with some embodiments of the present invention.
Figure 1B:
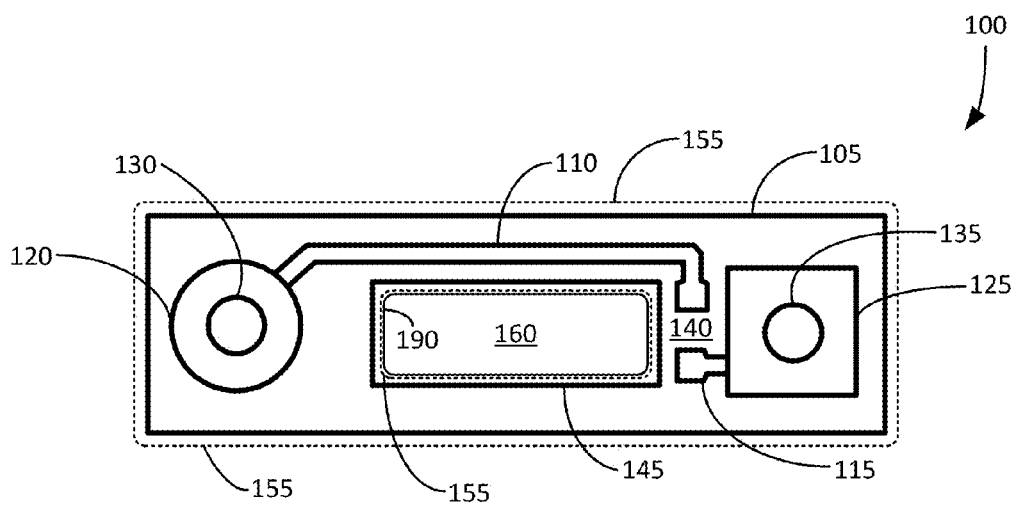
FIG. 1B illustrates a plan view of the molecular receptor-based CHEMFET of FIG. 1A.
Figure 1C:
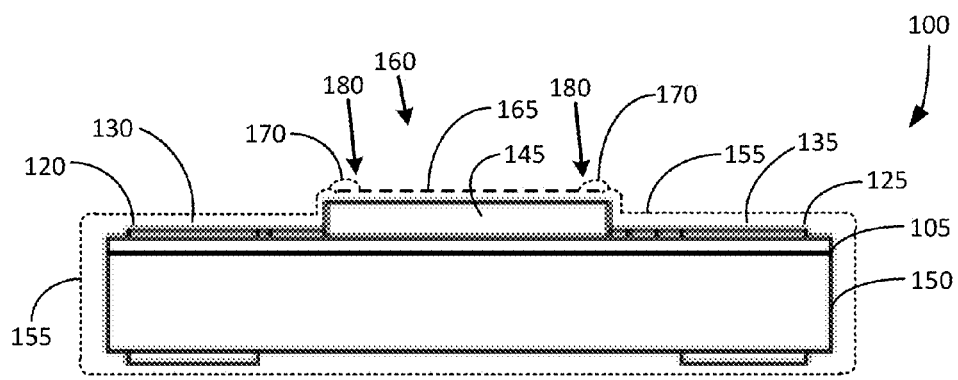
FIG. 1C illustrates a side elevation view of the molecular receptor-based CHEMFET of FIG. 1A, including a membrane and edge resin fasteners disposed on the gate thereof.
Figure 1D:
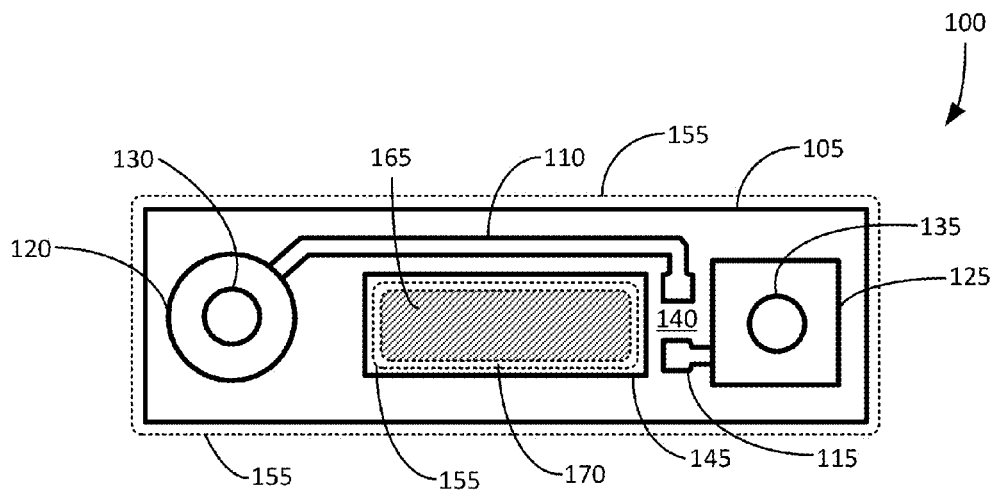
FIG. 1D illustrates a plan view of the molecular receptor-based CHEMFET of FIG. 1C.

FIG. 1A illustrates a side elevation view of a molecular receptor-based chemical field-effect transistor (CHEMFET) 100 in accordance with some embodiments of the present invention. FIG. 1B illustrates a plan view of the molecular receptor-based CHEMFET 100 of FIG. 1A. FIG. 1C illustrates a side elevation view of the molecular receptor-based CHEMFET 100 of FIG. 1A, including a membrane material 165 and edge resin fasteners 170 disposed on the gate thereof. FIG. 1D illustrates a plan view of the molecular receptor-based CHEMFET of FIG. 1C. Reference is now made to FIGS. 1A through 1D.

The CHEMFET 100 can be, for example, an ion-sensitive field-effect transistor (ISFET). The CHEMFET 100 can include a substrate 105, which can be connected (e.g., wire-bonded) to a printed circuit board (PCB) 150. A drain line 110 and source line 115 can be connected to bonding pads 120 and 125, respectively. Vias 130 and 135 can be formed in the bonding pads 120 and 125, respectively, through the substrate 105, for facilitating connections to drain and source pins, as further described below. Ends of the source line 115 and drain line 110 can be disposed adjacent one another, and proximate to a channel region 140. A voltage that is applied at or near the gate 145 causes an inversion layer to be formed in the channel region 140 between the ends of the source and drain lines, thereby creating a channel through which electrical current can pass. The channel can be ten (10) microns wide, or thereabout. Thus, an electrical current can be passed between the source and drain lines, which can be detected and measured. Feedback from an amplifier circuit (as further described below) can cause the electrical current to remain substantially constant to allow measurement of the changing gate voltage.

The substrate 105 can be pre-treated with between 2% and 30% $H_2O_2$, or thereabout, plasma etching, and/or functionalized with poly(hydroxyethyl-methacrylate). The gate 145 can include gate material of silicon nitride, aluminum oxide, and/or tantalum pentoxide. The PCB 150, source line 115, drain line 110, and/or other components disposed on the PCB 150, can be encapsulated by a first application (e.g., layer and/or portion) 155 of an impervious electrically insulative resin to cover the source and drain lines, and other components and wires, except for an exposed gate region 160. The exposed gate region 160 can initially be covered with a mask 190 during the first application 155 of the impervious electrically insulative resin, as shown in FIG. 1B. After the first application 155 of the impervious electrically insulative resin is applied, the mask 190 can be removed, thereby exposing substantially all of the gate region 160. In other words, the exposed gate region 160 is not encapsulated by the first application 155 of the impervious electrically insulative resin because the mask 190 prevents substantially all of the gate region 160 from coming into contact with the first application 155 of the electrically insulative resin.

Onto the exposed gate region 160 can be cast (e.g., by spin or drop coating) membrane material 165, as illustrated in FIGS. 1C and 1D. The membrane material 165 can also be cast onto at least some of the first application 155 of the electrically insulative resin.

The membrane material 165 can be prepared by mixing substances, and can include a mixture of substances. For example, the membrane material 165 can be prepared by mixing, and can include, a rubberized polymer such as a poly(acrylonitrile-cobutadiene) polymer, a non-specific ionophore such as tetraalkylammonium bromide or tetraalkylammonium nitrate, and/or a small-molecule receptor specific for the analyte of interest. The analyte of interest can include, for example, chloride, phosphate, perchlorate, potassium, lithium, or any suitable small molecule analyte. In some embodiments, the analyte of interest can have a molecular weight of 20 Daltons or thereabout.

A different alkyl-group (e.g., tetradecylammonium bromide) or a different counterion (e.g., tetraoctylammonium chloride or tetraoctylammonium nitrate) can be used in place of the non-specific ionophore (e.g., in place of tetraoctylammonium bromide). For example, the membrane material 165 can include a rubberized polymer such as a poly(acrylonitrile-cobutadiene) polymer, an alkyl-group (e.g., tetradecylammonium bromide), and/or a small-molecule receptor specific for the analyte of interest. By way of another example, the membrane material 165 can include a rubberized polymer such as a poly(acrylonitrile-cobutadiene) polymer, a counterion such as tetraoctylammonium chloride or tetraoctylammonium nitrate, and/or a small-molecule receptor specific for the analyte of interest.

By way of yet another example, the membrane material 165 can be prepared by mixing, or otherwise include a mixture of, 8% to 99% by weight, or thereabout, of poly(acrylonitrile-cobutadiene) polymer, 0.1% to 19% by weight, or thereabout, of tetraoctylammonium bromide or halide salt, and 0.1% to 10% by weight, or thereabout, of molecular receptor in tetrahydrofuran. Alternatively or in addition, other forms of tetraalkylammonium can be used, such as tetraheptyl, tetradecyl, chloride, bromide, and/or nitrate counterions.

By way of still another example, the membrane material 165 can be prepared by mixing, or otherwise include a mixture of, 94% to 96.7% by weight, or thereabout, of poly (acrylonitrile-cobutadiene) polymer, 3% to 5% by weight, or thereabout, of tetraoctylammonium bromide, and 0.3% to 1% by weight, or thereabout, of molecular receptor in tetrahydrofuran. The poly(acrylonitrile-cobutadiene) can include 39% by weight of acrylonitrile. The membrane material 165 can be deposited from slight variations in the solvent such as using acetonitrile instead of tetrahydrofuran.

After casting the membrane material 165 onto the exposed gate region 160, the membrane material 165 can be cured. The curing can include the application of heat-treatment and/or air-drying in a gas filled chamber. The gas within the chamber can be pressure-controlled. Alternatively, the application of heat-treatment and/or air-drying can be performed in normal atmosphere conditions. However, heat is not applied with tetrahydrofuran solution because bubbles can be formed, which can degrade the quality of the membrane material 165.

After the curing process, a second application (e.g., layer and/or portion) 170 of the impervious electrically insulative resin can be applied to secure the edges 180 of the membrane material 165 to the encapsulated substrate 105, thereby physically preventing lifting off of the membrane material 165 from the gate 145 of the CHEMFET 100 when, for example, the membrane material 165 is scratched or exposed to water. In other words, edge resin fasteners 170 can be applied to all edges (e.g., 180) of the membrane material 165 to secure the edges so that the membrane is resilient and robust, while continuing to function as a molecular receptor-based gate of the CHEMFET 100. The membrane material 165 can therefore be fixed to the substrate physically, via re-deposition of the impervious electrically insulative resin 170 on the edges 180 of the membrane material 165.

Figure 1E:
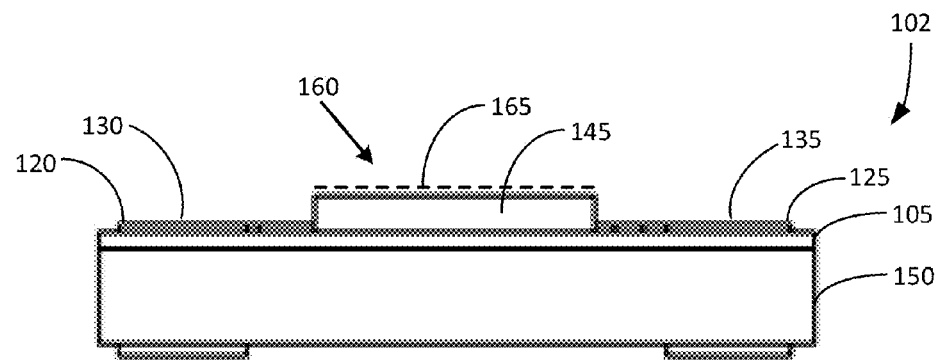
FIG. 1E illustrates a side elevation view of another example of a molecular receptor-based CHEMFET, including a membrane, in accordance with some embodiments of the present invention.
Figure 1F:
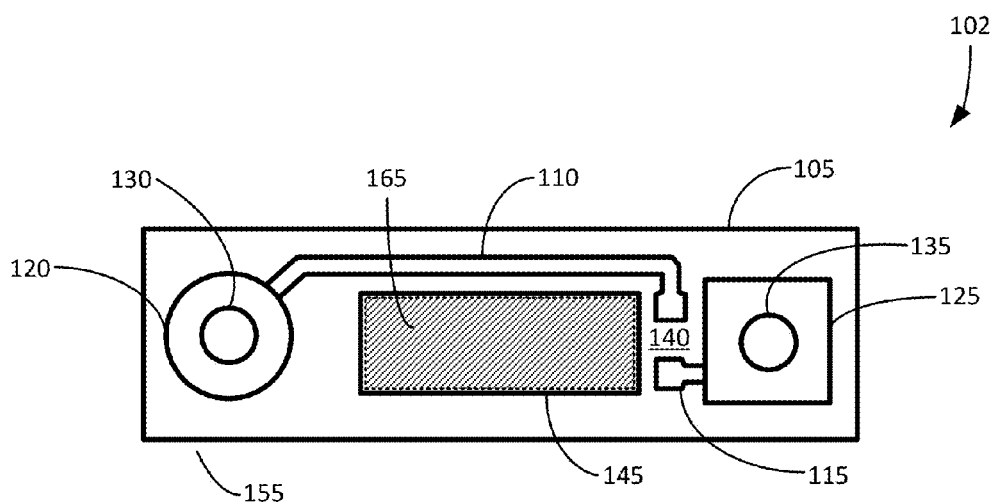
FIG. 1F illustrates a plan view of the molecular receptor-based CHEMFET of FIG. 1E.
Figure 1G:
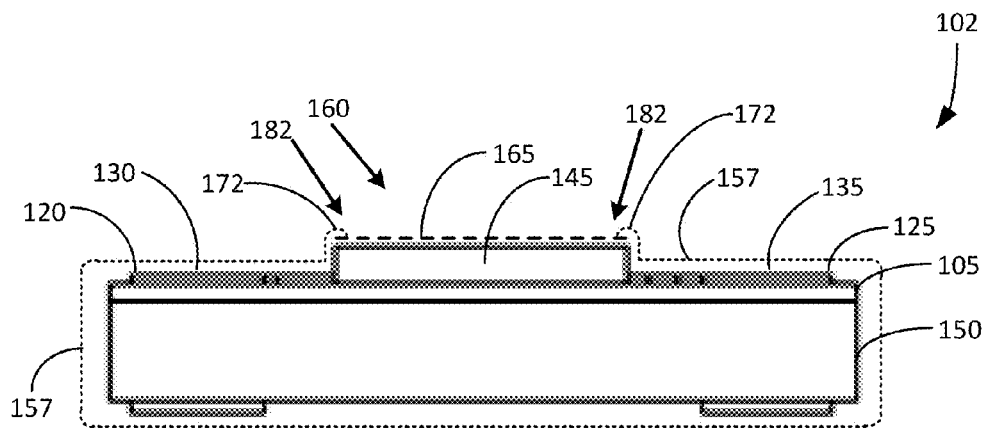
FIG. 1G illustrates a side elevation view of the molecular receptor-based CHEMFET of FIG. 1E, including the membrane and a single application of resin having edge resin fasteners disposed on the gate thereof.
Figure 1H:
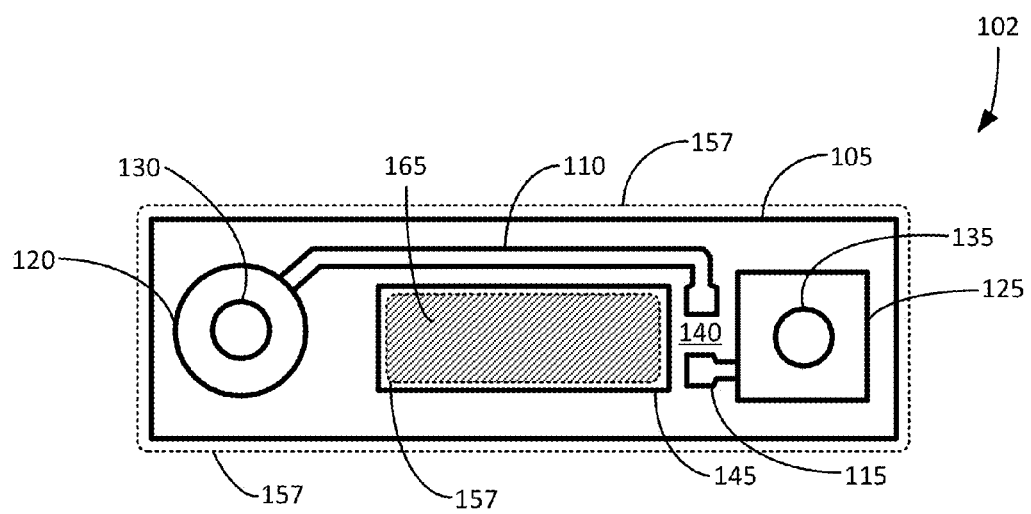
FIG. 1H illustrates a plan view of the molecular receptor-based CHEMFET of FIG. 1G.

FIG. 1E illustrates a side elevation view of a molecular receptor-based chemical field-effect transistor (CHEMFET) 102 in accordance with some embodiments of the present invention. FIG. 1F illustrates a plan view of the molecular receptor-based CHEMFET 102 of FIG. 1E. FIG. 1G illustrates a side elevation view of the molecular receptor-based CHEMFET 102 of FIG. 1E, including a membrane material 165 and a single application (e.g., layer) of resin 157 having edge resin fasteners 172 disposed on the gate thereof. FIG. 1H illustrates a plan view of the molecular receptor-based CHEMFET 102 of FIG. 1G. Reference is now made to FIGS. 1E through 1H.

The CHEMFET 102 can be, for example, an ion-sensitive field-effect transistor (ISFET). The CHEMFET 102 can include a substrate 105, which can be connected (e.g., wire-bonded) to a printed circuit board (PCB) 150. A drain line 110 and source line 115 can be connected to bonding pads 120 and 125, respectively. Vias 130 and 135 can be formed in the bonding pads 120 and 125, respectively, through the substrate 105, for facilitating connections to drain and source pins, as further described below. Ends of the source line 115 and drain line 110 can be disposed adjacent one another, and proximate to a channel region 140. A voltage that is applied at or near the gate 145 causes an inversion layer to be formed in the channel region 140 between the ends of the source and drain lines, thereby creating a channel through which electrical current can pass. The channel can be ten (10) microns wide, or thereabout. Thus, an electrical current can be passed between the source and drain lines, which can be detected and measured. Feedback from an amplifier circuit (as further described below) can cause the electrical current to remain substantially constant to allow measurement of the changing gate voltage.

The substrate 105 can be pre-treated with between 2% and 30% $H_2O_2$, or thereabout, plasma etching, and/or functionalized with poly(hydroxyethyl-methacrylate). The gate 145 can include gate material of silicon nitride, aluminum oxide, and/or tantulum pentoxide.

Onto the exposed gate region 160 can be cast (e.g., by spin or drop coating) membrane material 165, as illustrated in FIGS. 1E and 1F. The membrane material 165 can be prepared by mixing substances, and can include a mixture of substances. For example, the membrane material 165 can be prepared by mixing, and can include, a rubberized polymer such as a poly(acrylonitrile-cobutadiene) polymer, a non-specific ionophore such as tetraalkylammonium bromide or tetraalkylammonium nitrate, and/or a small-molecule receptor specific for the analyte of interest. The analyte of interest can include, for example, chloride, phosphate, perchlorate, potassium, lithium, or any suitable small molecule analyte. In some embodiments, the analyte of interest can have a molecular weight of 20 Daltons or thereabout.

A different alkyl-group (e.g., tetradecylammonium bromide) or a different counterion (e.g., tetraoctylammonium chloride or tetraoctylammonium nitrate) can be used in place of the non-specific ionophore (e.g., in place of tetraoctylammonium bromide). For example, the membrane material 165 can include a rubberized polymer such as a poly(acrylonitrile-cobutadiene) polymer, an alkyl-group (e.g., tetradecylammonium bromide), and/or a small-molecule receptor specific for the analyte of interest. By way of another example, the membrane material 165 can include a rubberized polymer such as a poly(acrylonitrile-cobutadiene) polymer, a counterion such as tetraoctylammonium chloride or tetraoctylammonium nitrate, and/or a small-molecule receptor specific for the analyte of interest.

By way of yet another example, the membrane material 165 can be prepared by mixing, or otherwise include a mixture of, 8% to 99% by weight, or thereabout, of poly(acrylonitrile-cobutadiene) polymer, 0.1% to 19% by weight, or thereabout, of tetraoctylammonium bromide or halide salt, and 0.1% to 10% by weight, or thereabout, of molecular receptor in tetrahydrofuran. Alternatively or in addition, other forms of tetraalkylammonium can be used, such as tetraheptyl, tetradecyl, chloride, bromide, and/or nitrate counterions.

By way of still another example, the membrane material 165 can be prepared by mixing, or otherwise include a mixture of 94% to 96.7% by weight, or thereabout, of poly(acrylonitrile-cobutadiene) polymer, 3% to 5% by weight, or thereabout, of tetraoctylammonium bromide, and 0.3% to 1% by weight, or thereabout, of molecular receptor in tetrahydrofuran. The poly(acrylonitrile-cobutadiene) can include 39% by weight of acrylonitrile. The membrane material 165 can be deposited from slight variations in the solvent such as using acetonitrile instead of tetrahydrofuran.

After casting the membrane material 165 on to the exposed gate region 160, the membrane material 165 can be cured. The curing can include the application of heat-treatment and/ or air-drying in a gas filled chamber. The gas within the chamber can be pressure-controlled. Alternatively, the application of heat-treatment and/or air-drying can be performed in normal atmosphere conditions. However, heat is not applied with tetrahydrofuran solution because bubbles can be formed, which can degrade the quality of the membrane material 165.

After the curing process, a single contiguous application of impervious electrically insulative resin 157 can be applied to simultaneously encapsulate the PCB 150 and secure the edges 182 of the membrane material 165, thereby physically preventing lifting off of the membrane material 165 from the gate 145 of the CHEMFET 102 when, for example, the membrane material 165 is scratched or exposed to water. In other words, edge resin fasteners 172 can be part of the single application of electrically insulative resin 157, and can be applied to all edges (e.g., 182) of the membrane material 165 to secure the edges so that the membrane is resilient and robust. In other words, the edges 182 of the membrane material 165 can be secured and sealed with the single application of electrically insulative resin 157, which also forms a potting or encapsulation of the CHEMFET 102.

Figure 1I:
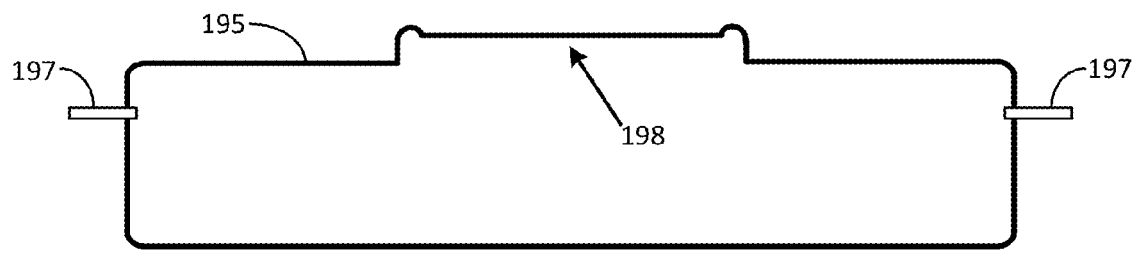
FIG. 1I illustrates an example of a mold for applying impervious electrically insulative resin in accordance with some embodiments of the present invention.

The PCB 150, source line 115, drain line 110, and/or other components disposed on the PCB 150, can be encapsulated by the single application of the impervious electrically insulative resin 157. The exposed gate region 160 is not encapsulated by the single application of the impervious electrically insulative resin 157 because one or more molds (e.g., as shown in FIG. 1I below) prevents substantially all of the gate region 160 from coming into contact with the single application 157 of the electrically insulative resin 157. This ensures reliable function as a molecular receptor-based gate of the CHEMFET 102. The membrane material 165 can therefore be fixed to the substrate physically, via deposition of the impervious electrically insulative resin 172 on the edges 182 of the membrane material 165.

FIG. 1I illustrates an example of a mold 195 for applying impervious electrically insulative resin in accordance with some embodiments of the present invention. The shape of the mold 195 can conform to the general shape of the CHEMFET 100/102. It will be understood that minor variations in the shape of the mold still fall within the scope of the disclosed embodiments. The mold 195 can include one or more insertion members 197 for inserting the electrically insulative resin 157 into the mold 195. The mold 195 can surround the CHEMFET 100 or 102. For example, the mold 195 can surround the CHEMFET 102 while protecting the exposed gate region 160 so that the single application of resin 157 having edge resin fasteners 172 can be disposed on the edges 182 of the membrane material 165 and other components of the CHEMFET 102, but not on the exposed gate region 160 thereof. For example, the lower surface 198 of the mold 195 can be in contact with the upper surface of the exposed gate region 160 when inserting the single application of resin 157, thereby protecting the exposed gate region 160 from the application of the resin. In some embodiments, the mold 195 need not entirely surround the CHEMFET 102, but rather, the mold can cover at least a portion of the CHEMFET 102. In some embodiments, the mold can comprise 65% dimethyl siloxane, or thereabout, 17% silica (i.e., crystalline quartz), or thereabout, 9% Thixatrol ST, or thereabout, 4% polydimethylsiloxane, or thereabout, 1% decamethyl cyclopentasiloxane, or thereabout, 1% glycerine, or thereabout, and 1% titanium dioxide, or thereabout.

Figure 2A:
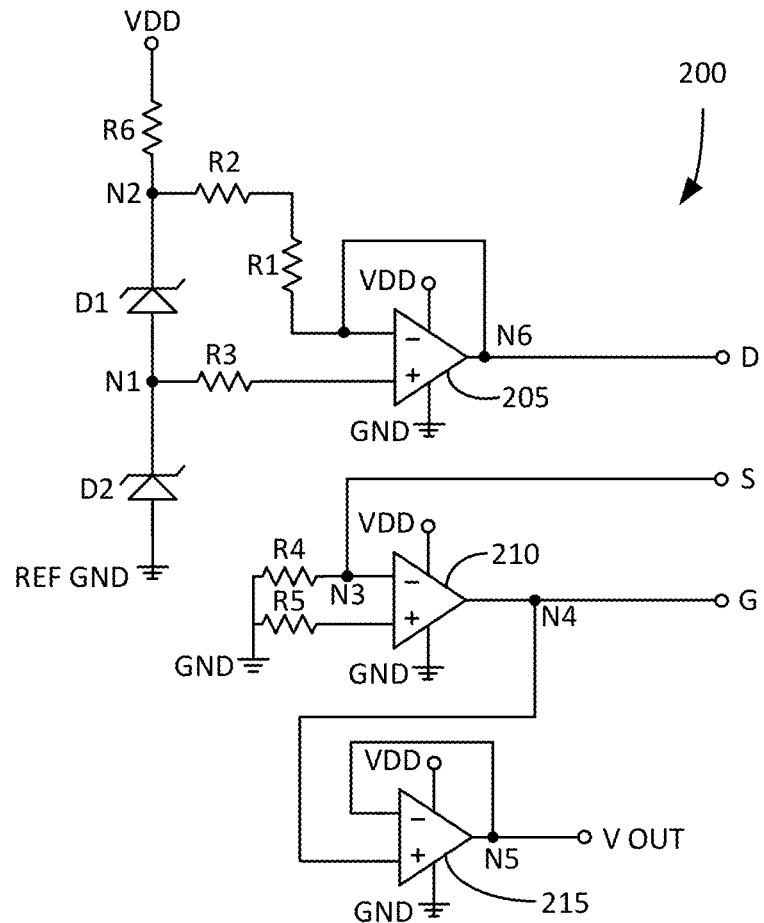
FIG. 2A illustrates an example circuit diagram of an amplifier for use with the molecular receptor-based CHEMFET of FIGS. 1A through 1D or with the molecular receptor-based CHEMFET 102 of FIGS. 1E through 1H.
Figure 2B:
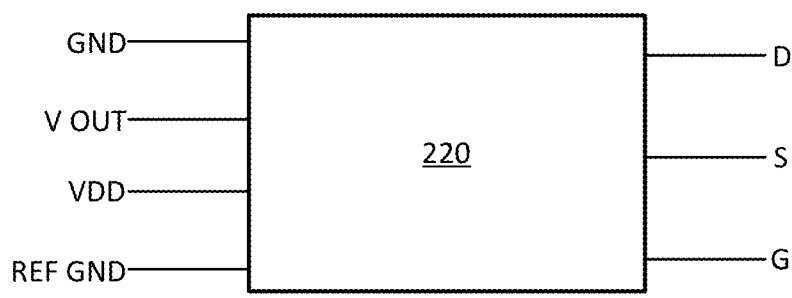
FIG. 2B illustrates a package of the amplifier circuit of FIG. 2A.

FIG. 2A illustrates an example circuit diagram of an amplifier 200 for use with the molecular receptor-based CHEMFET 100 of FIGS. 1A through 1D or with the molecular receptor-based CHEMFET 102 of FIGS. 1E through 1H. FIG. 2B illustrates a high level block diagram of the amplifier circuit of FIG. 2A. Reference is now made to FIGS. 2A and 2B.

It will be understood that while certain voltage sources, resistors, and other circuit components associated with some embodiments are shown, other suitable voltage sources, resistors, and other circuit components can be used. As can be seen, the amplifier circuit 200 includes a variety of resistors (e.g., R1, R2, R3, R4, R5, and R6), Zener diodes (e.g., D1 and D2), differential operational amplifiers (e.g., op amps 205, 210, and 215), power supply terminals (e.g., VDD), and floating ground terminals (e.g., GND). The terminal labeled 'D' can be coupled to the drain line 110 (of FIG. 1A). The terminal labeled 'S' can be coupled to the source line 115 (of FIG. 1A). The terminal labeled 'G' can be coupled to the gate 145 (of FIG. 1A). A reference ground (REF GND) terminal can be coupled to one or more (e.g., four) sensor pins, as further described below. Floating ground (GND) terminals can be coupled to a voltage source (e.g., battery), as also further described below. The terminal labeled "V OUT" is an output terminal providing an amplified output voltage. The amplified output voltage is an indicator of the quantity of nitrate levels in field ground soil.

In some embodiments, R1 can be 4.3 kilo-ohms (kΩ), or thereabout, R2 can be 10 kΩ, or thereabout, R3 can be 4.3 kΩ, or thereabout, R4 can be 50 kΩ, or thereabout, R5 can be 27 kΩ, or thereabout, and R6 can be 2 kΩ, or thereabout. In some embodiments, VDD can be +5 Volts (V), or thereabout. In some embodiments, Zener diodes D1 and D2 can each have a Zener breakdown voltage of 1.2 V, or thereabout.

R3 can be coupled between the op amp 205 and node N1. D2 can be coupled to the node N1 and the reference ground REF GND terminal. D1 can be coupled to node N2 and the node N1. R6 can be coupled to VDD and the node N2. R1 and R2 can be coupled in series between the node N2 and the op amp 205. R4 can be coupled between node N3 and a floating ground (GND) terminal. R5 can be coupled between the op amp 210 and a floating ground (GND) terminal.

The terminal D of the op amp 205 can be coupled to the drain (e.g., drain line 110) of the CHEMFET 100 (of FIG. 1A) or the CHEMFET 102 (of FIG. 1E). The terminal S can be coupled to node N3 of the op amp 210, and to the source (e.g., source line 115) of the CHEMFET 100 (of FIG. 1A) or the CHEMFET 102 (of FIG. 1E). The terminal G of the op amp 210 can be coupled to the gate (e.g., gate 145) of the CHEMFET 100 (of FIG. 1A) or the CHEMFET 102 (of FIG. 1E). Node N4 can couple the terminal 'G' of the op amp 210 to an input of the op amp 215. The output V OUT of the op amp 215 and an input of the op amp 215 can be coupled to node N5. Similarly, the terminal 'D' the op amp 205 and an input of the op amp 205 can be coupled to node N6.

The amplifier circuit 200 can be packaged within a package 220, as shown in FIG. 2B. As can be seen, the package 220 can include terminals for connecting to a power supply (e.g., +5 Volts), an output (e.g., V OUT), a reference ground (REF GND) terminal, and a floating ground (GND) terminal. In addition, the package 220 can include terminals G, S, and D for connecting to gate (145), source line (115), and drain line (110), respectively, of the CHEMFET 100 (of FIG. 1A) or the CHEMFET 102 (of FIG. 1E).

Figure 3A:
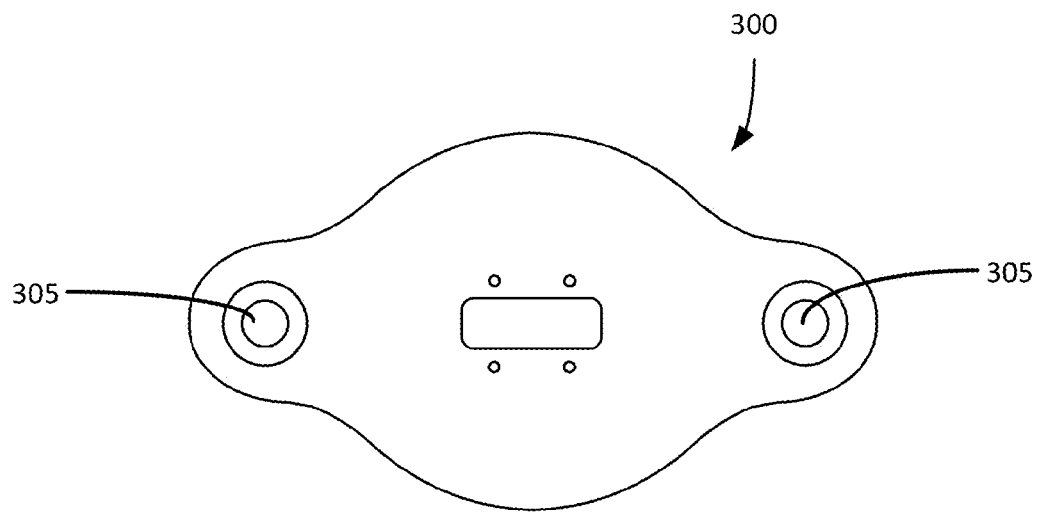
FIGS. 3A and 3B illustrate a sensor housing in which the CHEMFET and the amplifier circuit and other components are contained, in accordance with some embodiments of the present invention.
Figure 3B:
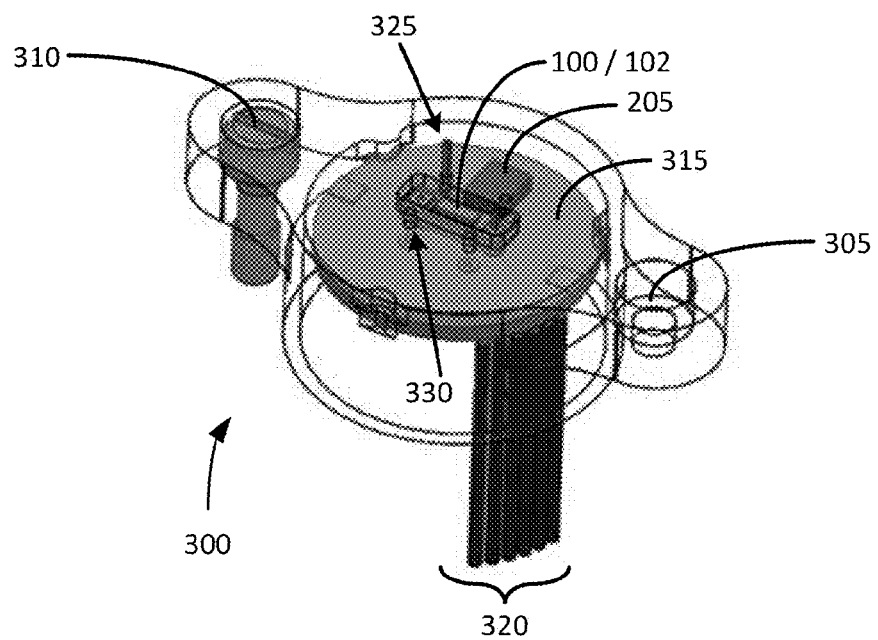
Figure 3C:
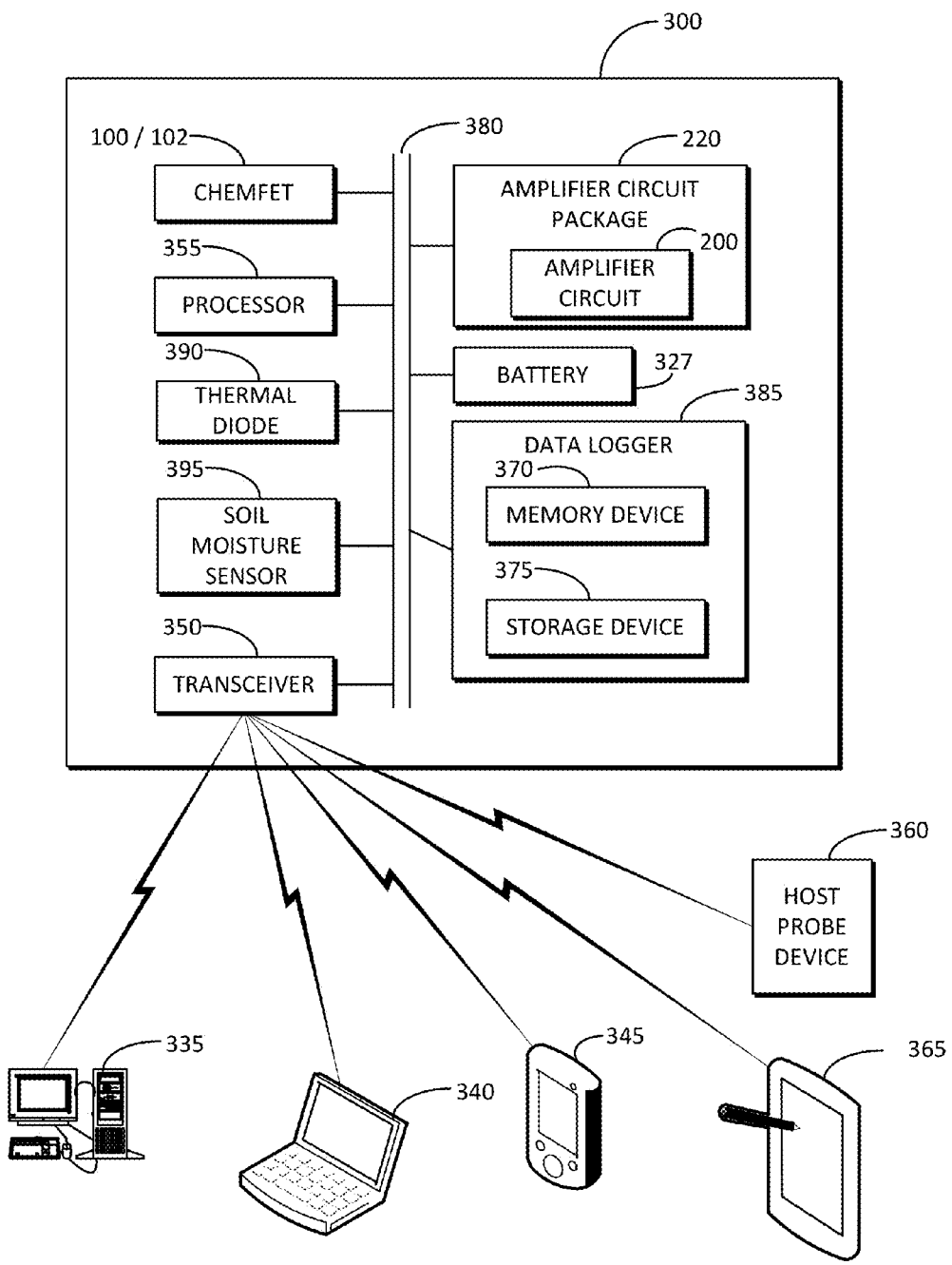
FIG. 3C illustrates a schematic block diagram of the of the sensor housing including various components disposed therein, within a larger system of external computing devices, in accordance with some embodiments of the present invention.

FIGS. 3A through 3C illustrate a sensor housing 300 in which the CHEMFET 100 or the CHEMFET 102, and other components such as the amplifier circuit package 220 are contained, in accordance with some embodiments of the present invention. FIG. 3A is a plan view of the sensor housing 300. FIG. 3B is a partially transparent perspective view of the sensor housing 300, including various components disposed therein. FIG. 3C illustrates a schematic block diagram of the of the sensor housing 300 including various components disposed therein, within a larger system of external computing devices (e.g., 335, 340, and 345), in accordance with some embodiments of the present invention. Reference is now made to FIGS. 3A through 3C.

Figure 6:
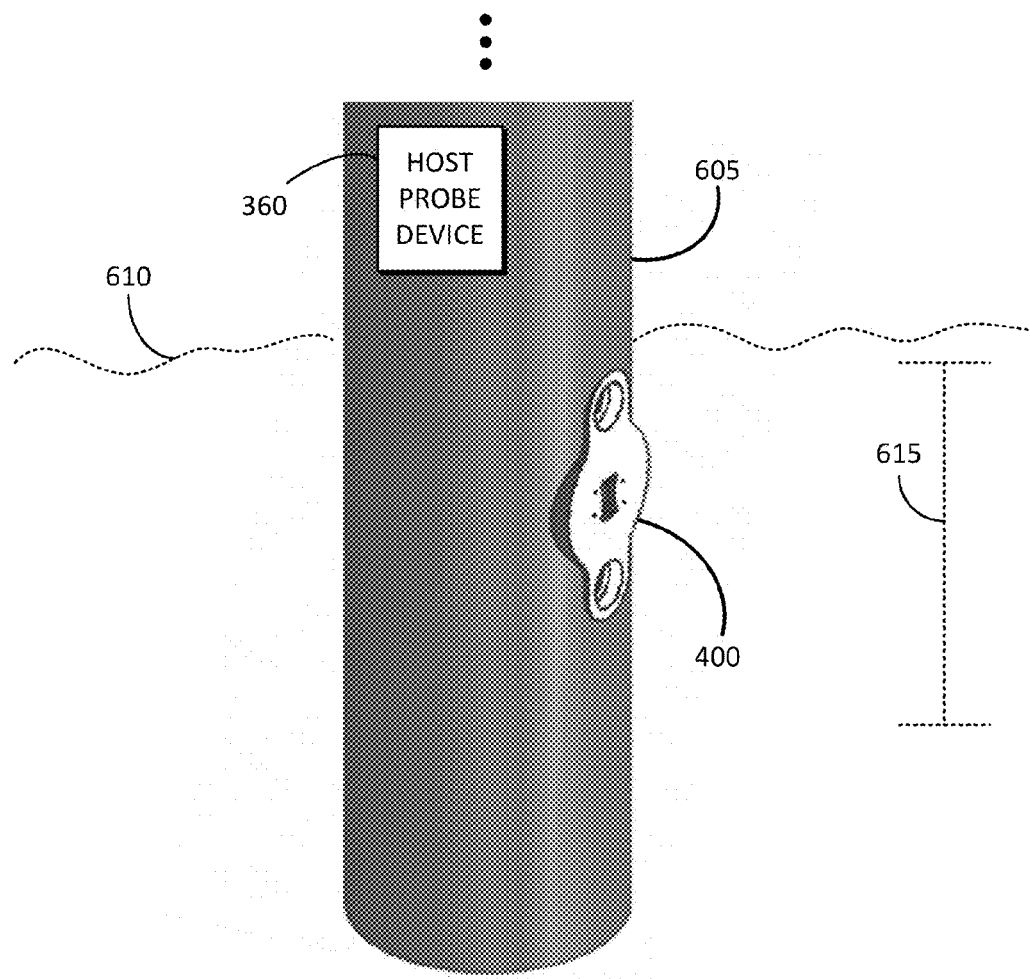
FIG. 6 illustrates a probe body including the sensor module of FIGS. 1A through 5 inserted therein, in accordance with some embodiments of the present invention.

The sensor housing 300 can include one or more openings (e.g., 305) through which the sensor housing 300 can be secured to a probe body (as illustrated in FIG. 6 below), which can be inserted into the field ground soil (as also illustrated in FIG. 6 below). For example, one or more screws (e.g., 310 of FIG. 3B) can be inserted through the corresponding one or more openings 305 to secure the sensor housing 300. As can be seen in FIG. 3B, the CHEMFET 100/102 and the amplifier package 220 can be mounted on a surface 315 within the sensor housing 300. One or more sensor pins (e.g., 325) can be coupled to the reference ground (REF GND) terminal. The one or more sensor pins 325 can protrude externally from the sensor housing 300 to make direct contact with the field ground soil. The one or more sensor pins 325 can be secured to the sensor housing 300 through corresponding openings 330 in the surface 315. In some embodiments, there are four (4) individual sensor pins 325, each of which can be electrically united and coupled to the reference ground (REF GND) terminal of the amplifier circuit 200 (of FIG. 2A).

In some embodiments, the one or more sensor pins 325 are spring loaded for flexibly interfacing with or otherwise contacting the field ground soil. In some embodiments, the one or more sensor pins 325 are gold plated to prevent oxidation. The sensor housing 300 can be held in place in the field ground soil geometrically with respect to the sensor pins 325 to reduce changes in current path and effects from the resistivity and/or electrical conductivity changes in the field ground soil. The sensor pins 325 can be of a specific size, range of sizes, and/or position relative to the exposed gate region 160 of the CHEMFET 100/102. For example, each sensor pin 325 can be between 10 to 15 millimeters (mm) in length, or thereabout. Moreover, each sensor pin 325 can be positioned within a radius of 5 mm, or thereabout, from the exposed gate region 160 of the CHEMFET 100/102.

In addition, one or more conductors, such as wires 320, can be used to transmit and receive information to and from one or more components contained within the sensor housing 300. Alternatively, the information can be transmitted and received wirelessly as further described below, and in such case, the wires 320 can be omitted. The transmitted information can include field ground soil nitrate level information or the like. The received information can include operational instructions or the like. Alternatively or in addition, the wires 320 can provide the power supply (e.g., VDD) and/or the ground (GND) terminals, and in such case, a battery is not needed.

FIG. 3C illustrates a schematic system block diagram of the sensor housing 300, which can contain the CHEMFET 100/102 and the amplifier circuit package 220 including the amplifier circuit 200. In addition, the sensor housing 300 can contain a transceiver 350 for interfacing with external and/or remote devices such as computer 335, laptop 340, smart phone 345, tablet 365, and/or a host probe device 360. For example, a user of the computer 335, laptop 340, smart phone 345, and/or tablet 365, can access nitrate level information by communicating with the transceiver 350 via wires 320 and/or wirelessly. The transceiver 350 can be a near field communications chip (NFC). By way of another example, the host probe device 360 can be partially or fully contained within a same probe (not shown) as the sensor housing 300, as further described below. One or more components within the sensor housing 300 can communicate with one or more components within the host probe device 360 via wires 320 and/or wirelessly.

The sensor housing 300 can further include a battery 327 and a processor 355 and/or data logger 385. The data logger 385 can include a memory device 370 and/or other suitable storage device 375 for storing field ground soil nitrate level information over a period of time. Two or more of the various components within the sensor housing 300 can be communicatively coupled to each other via bus 380.

A single sensor housing (e.g., 300) can include the CHEMFET 100/102, the amplifier package 220, the data logger or data acquisition unit 385, and the transceiver 350, for connection to a personal computer 335 and/or other suitable external computing device (e.g., 340, 345, 365). The housing can be 30 centimeters (cm) in width and 20 cm deep, or thereabout. Alternatively or in addition, the sensor housing 300 can include external electrical conductivity and/or connectivity, a thermal diode 390, and/or a soil moisture sensor 395 in a slightly larger housing, which can be more useful for home and garden use.

Figure 4:
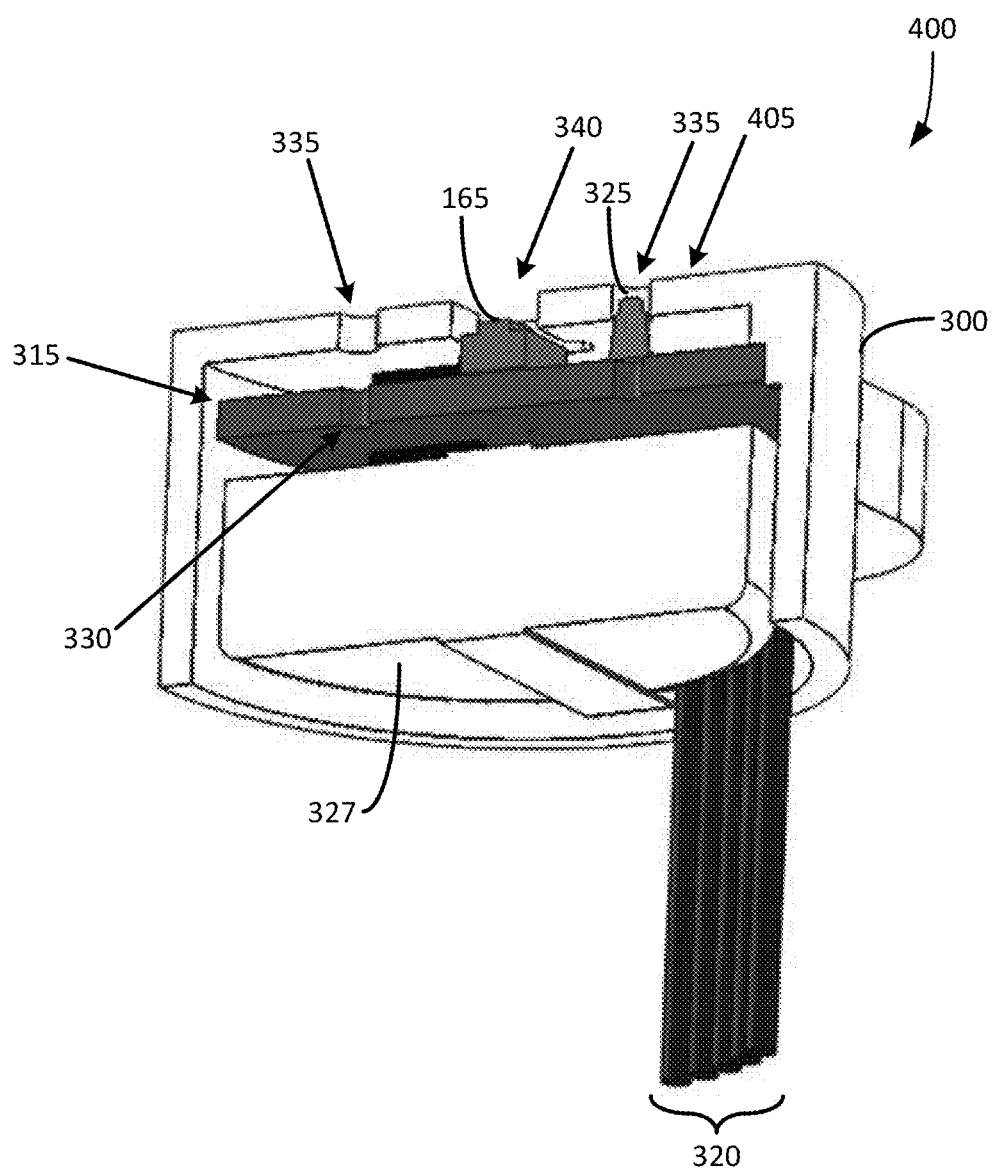
FIG. 4 illustrates a cross sectional view of a sensor module including the sensor housing of FIGS. 3A and 3B, and including various components contained therein.

FIG. 4 illustrates a cross sectional view of a sensor module 400, including the sensor housing 300 of FIGS. 3A and 3B, the various components contained in the sensor housing, and/or the wires 320. A battery 327 can be disposed adjacent to a back side of the mounting surface 315, and can be potted and/or substantially encapsulated with impervious electrically insulative resin (not shown) to prevent ingress of water. The battery 327 can provide the necessary operational energy (e.g., VDD) to the CHEMFET 100/102, the amplifier circuit 200, and/or other components contained within the sensor housing 300. The battery 327 can also provide the floating ground (GND) to one or more floating ground terminals described herein. The sensor housing 300 can include openings 335 through which the sensor pins (e.g., 325) can protrude into the field ground soil. An end of the sensor pin 325 can be recessed relative to an outer surface 405 of the sensor housing 300. It will be understood, however, that the sensor pin 325 can be flush with or extend outwardly beyond the outer surface 405 to make contact with the field ground soil. In addition, the sensor housing 300 can include a gate opening 340 exposing the membrane material 165 of the gate 145 to the field ground soil.

Figure 5:
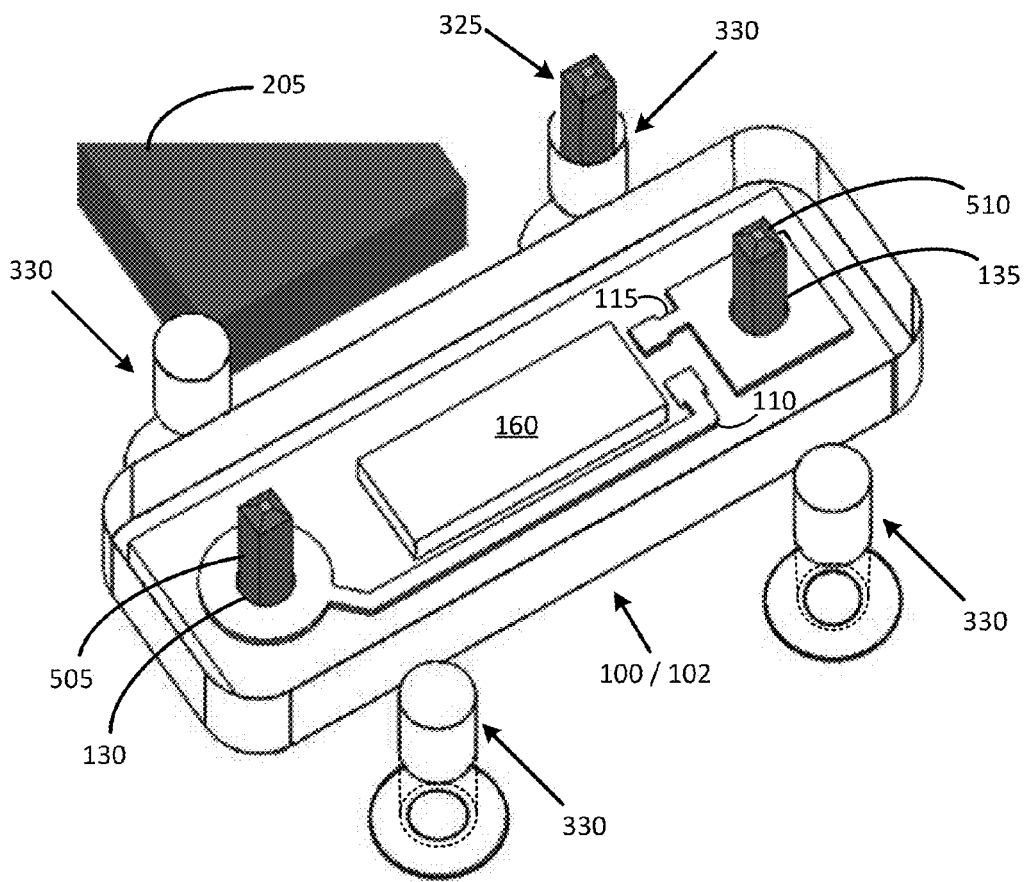
FIG. 5 illustrates perspective close-up view of the molecular receptor-based CHEMFET of FIGS. 1A through 1D or with the molecular receptor-based CHEMFET of FIGS. 1E through 1H including various pins in accordance with some embodiments of the present invention.

FIG. 5 illustrates a perspective close-up view of the molecular receptor-based CHEMFET 100 of FIGS. 1A through 1D or the CHEMFET 102 of FIGS. 1E through 1H, which can be disposed within the sensor housing 300. The sensor housing 300 can include sensor pins (e.g., 325). The sensor pins (e.g., 325) can be inserted in corresponding openings (e.g., 330) in the sensor housing 300. The sensor housing 300 can also include a drain pin (e.g., 505) and a source pin (e.g., 510). The drain pin 505 can be disposed through the via 130 and electrically coupled to the drain line 110. Similarly, the source pin 510 can be disposed through the via 135 and electrically coupled to the source line 115. The drain pin 505 can be coupled to the drain terminal 'D' of the amplifier circuit 200 (of FIG. 2A). The source pin 510 can be coupled to the source terminal 'S' of the amplifier circuit 200 (of FIG. 2A). The gate 145 can be coupled to the gate terminal 'G' of the amplifier circuit 200 (of FIG. 2A).

The sensor module 400, the sensor housing 300, and/or one or more of its components can be calibrated in solutions of constant ionic strength and varying nitrate concentration. The calibration parameters can be flashed to an on-board storage device (e.g., memory device 370 and/or storage device 375 of FIG. 3C). Such calibration can take place at the site of manufacturing and/or assembly. Alternatively, such calibration can take place in the field before or after deploying the sensor module 400 or inserting the sensor module 400 into the field ground soil.

FIG. 6 illustrates a probe body 605 including the sensor module 400 of FIGS. 1A through 5 inserted therein, in accordance with some embodiments of the present invention. The sensor module 400 can be installed and/or contained partially or fully into the probe body 605 for insertion into the field ground soil 610. The probe body 605 can include one or more sensor modules 400. The probe body 605 can be made of, for example, a polyvinyl chloride (PVC) pipe or any other suitable probe material capable of receiving the sensor module 400 and capable of being inserted into the field ground soil 610.

The sensor module 400 can include or otherwise interface with the host probe device 360, which can be contained partially or fully within the probe body 605. The sensor module 400 can be separate from the host probe device 360. In other words, the host probe device 360 can be external to the sensor module 400. The sensor module 400 can wirelessly interface with the host probe device 360 using one or more transceivers (e.g., near field communications chips (NFC)) for data transfer to and from the host probe. The wireless feature avoids breaking the seal between the field ground soil and internal electronics in both the sensor module 400 and the host probe 605 any more than necessary, and allows for easy access for recalibration and/or replacement of the nitrate sensor portion. In some embodiments, the sensor module 400 can communicate directly with a smart phone (e.g., 345 of FIG. 3C) and/or tablet (e.g., 365 of FIG. 3C) via the NFC, Bluetooth® protocol, cellular link, and/or other suitable short-range or long-range wireless interface. In some embodiments, the host probe device 360 can provide electrical conductivity, pH data, and/or temperature data that the sensor data can be calibrated against. The host probe device 360 can include one or more NFC chips for receiving data or instructions from and/or sending data or instructions to the one or more NFC chips of the sensor module 400.

Multiple probe bodies 605, along with sensor modules 400, can be installed in field soils at varying depths, typically in the root zone 615 (i.e., top of root to bottom of root). In other words, the sensor module 400 can be installed at a depth within the field ground soil that is between a top of the root zone 615 and a bottom of the root zone 615. In addition, the probe body 605 can be installed below the root zone 615. Alternatively, a single probe body 605 can include multiple sensor modules 400, each sensor module 400 spaced apart within the root zone 615, and/or below the root zone 615. This allows for data collection, by a first sensor module 400, of the nitrate gradient in the field ground soil in the active area of plant uptake 615, and a second sensor module (not shown) below the active area 615 that serves as an alert system when the field is either over-fertilized, over watered, and/or the soil nitrate is washing below the reach of the plants' roots.

Figure 7:
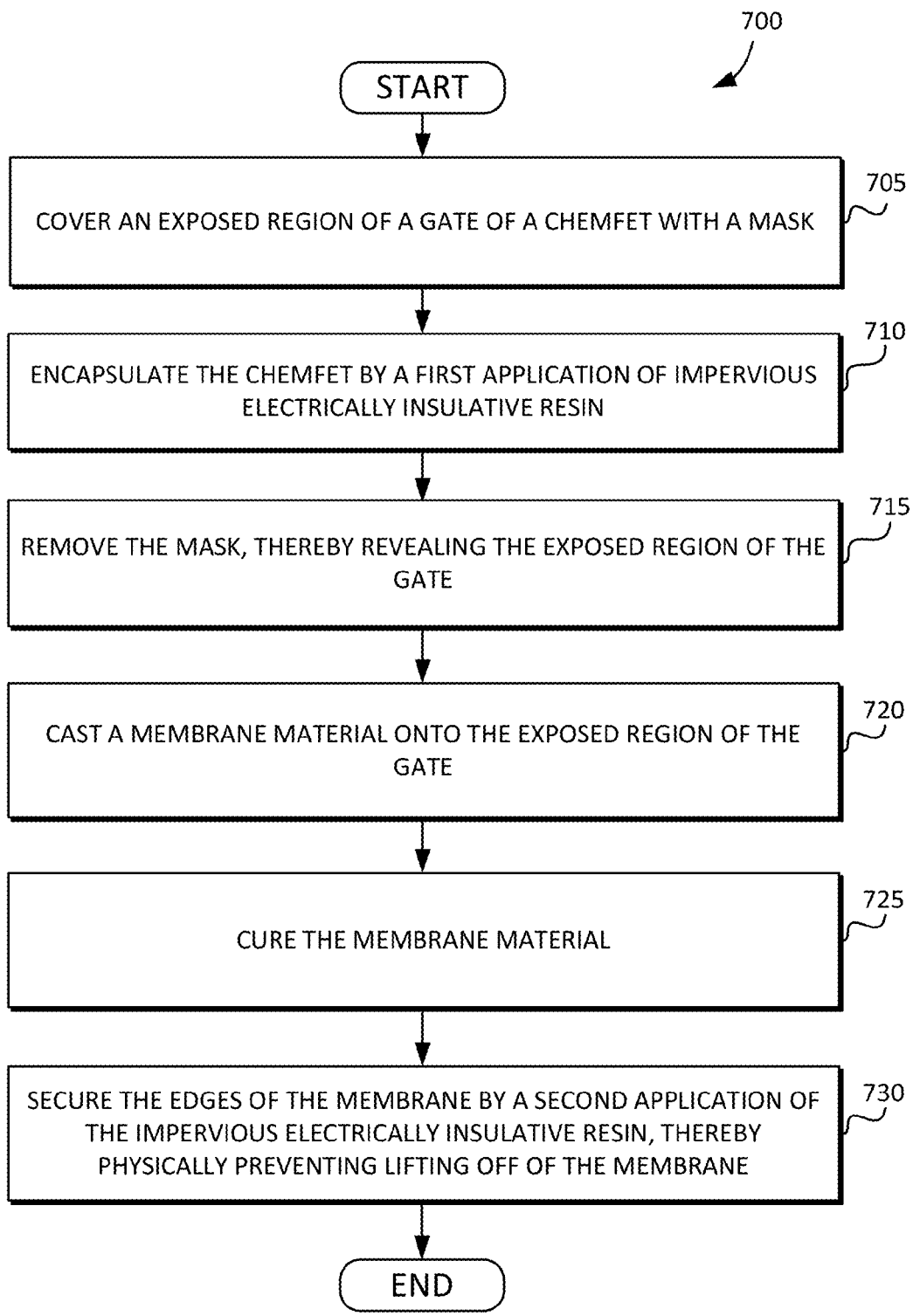
FIG. 7 is a flow diagram illustrating a technique for securing a membrane using impervious electrically insulative resin, in accordance with some embodiments of the present invention.

FIG. 7 is a flow diagram 700 illustrating a technique for securing a membrane using impervious electrically insulative resin, in accordance with some embodiments of the present invention. The technique begins at 705, where an exposed region of the gate of the CHEMFET can be covered with a mask. The flow proceeds to 710, where the CHEMFET can be encapsulated by a first application (e.g., layer and/or portion) of impervious electrically insulative resin. At 715, the mask can be removed, thereby revealing the exposed region of the gate. At 720, a membrane material having the composition described above can be cast onto the exposed region of the gate. At 725, the membrane can be cured. The flow continues to 730, where the edges of the membrane are secured by a second application (e.g., layer and/or portion) of the impervious electrically insulative resin, thereby physically preventing lifting off of the membrane.

Figure 8:
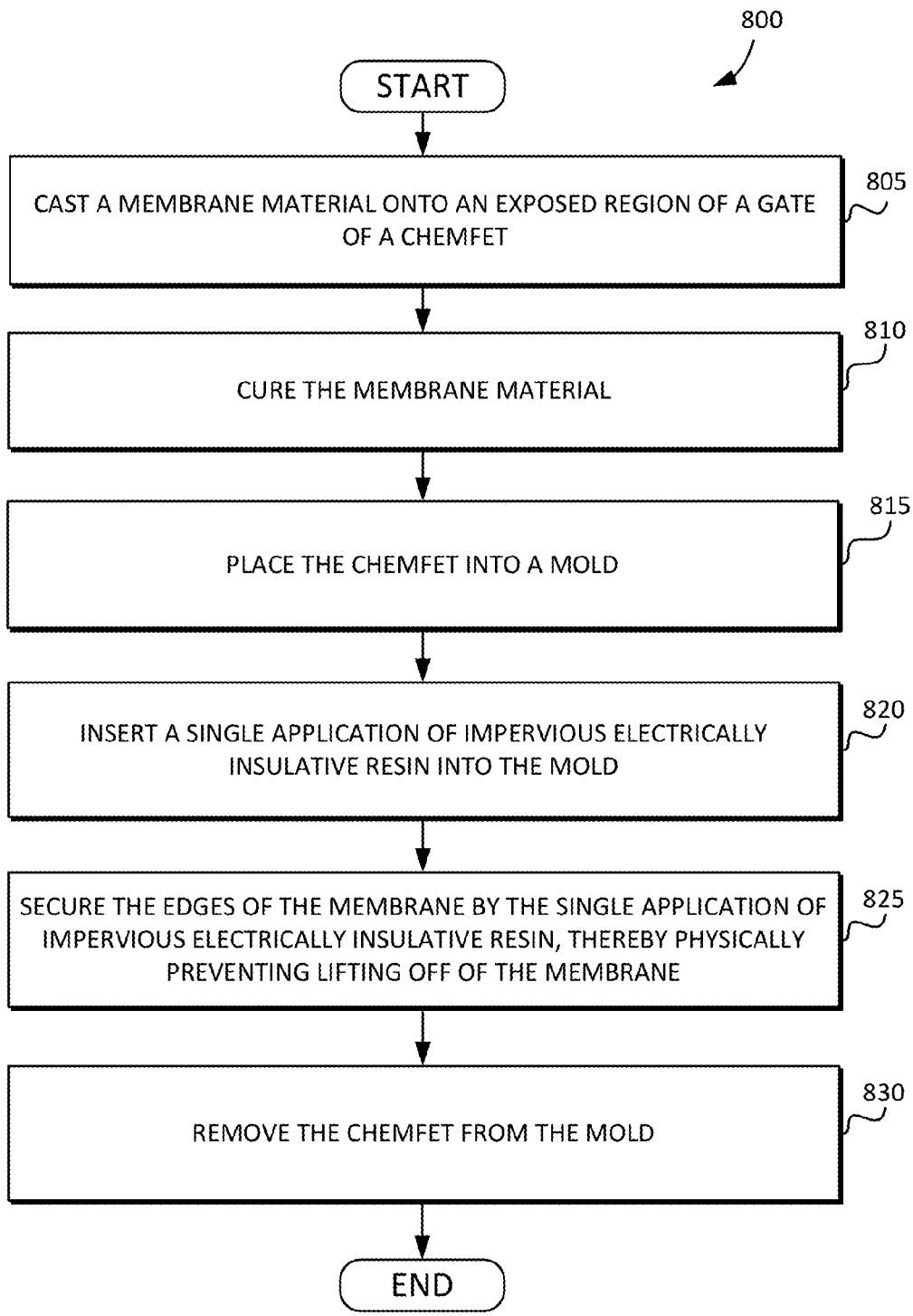
FIG. 8 is a flow diagram illustrating another technique for securing a membrane using impervious electrically insulative resin, in accordance with some embodiments of the present invention.

FIG. 8 is a flow diagram 800 illustrating a technique for securing a membrane using impervious electrically insulative resin, in accordance with some embodiments of the present invention. The technique begins at 805, a membrane material having the composition described above can be cast onto the exposed region of the gate. At 810, the membrane can be cured. The flow continues to 815, where the CHEMFET can be placed in a mold. At 820, a single contiguous application of impervious electrically insulative resin can be inserted into the mold. At 825, the edges of the membrane are secured by the single application of the impervious electrically insulative resin, thereby physically preventing lifting off of the membrane. At 830, the CHEMFET can be removed from the mold.

The sensor module 400 provides a real-time monitoring system during field fertilization, irrigation, and/or fertigation. The sensor module 400 provides the ability to cause an alert in response to nitrate efflux below the root zone of the plants, as this is indicative of over-fertilization and/or watering, and thus prevents wasteful application and the downstream ecological consequences of the non point-source pollution typically generated from large agricultural fields.

The sensor module 400 provides a molecular receptor with a thermodynamic affinity for nitrate, which improves its selectivity over the common intereferent in field soils (i.e., chloride) and thus its accuracy. Prior to the development of the various embodiments described herein, the lack of a nitrate selective membrane with high selectivity for nitrate over chloride precluded the adoption of these types of technologies for in-soil measurement.

The various embodiments of the invention described herein can be used to provide real-time fertigation monitoring, soil testing, and/or greenhouse monitoring. Additional uses include real-time wastewater monitoring, well-water monitoring, tiling, or effluent monitoring during re-treatment in closed-flow systems (e.g., hydroponics or tiled nurseries). Embodiments of the invention, as described herein, provide improved profits to farmers through resource optimization. Because the sensor module 400 can be remotely accessed and controlled, less labor needs to be devoted to nitrate monitoring. In addition, increased consistency of capital-input-to-yield year over year is provided. Moreover, government penalties can be lowered.

The following discussion is intended to provide a brief, general description of a suitable machine or machines in which certain aspects of the invention can be implemented. Typically, the machine or machines include a system bus to which is attached processors, memory, e.g., random access memory (RAM), read-only memory (ROM), or other state preserving medium, storage devices, a video interface, and input/output interface ports. The machine or machines can be controlled, at least in part, by input from conventional input devices, such as keyboards, mice, etc., as well as by directives received from another machine, interaction with a virtual reality (VR) environment, biometric feedback, or other input signal. As used herein, the term "machine" is intended to broadly encompass a single machine, a virtual machine, or a system of communicatively coupled machines, virtual machines, or devices operating together. Exemplary machines include computing devices such as personal computers, workstations, servers, portable computers, handheld devices, telephones, tablets, etc., as well as transportation devices, such as private or public transportation, e.g., automobiles, trains, cabs, etc.

The machine or machines can include embedded controllers, such as programmable or non-programmable logic devices or arrays, Application Specific Integrated Circuits (ASICs), embedded computers, smart cards, and the like. The machine or machines can utilize one or more connections to one or more remote machines, such as through a network interface, modem, or other communicative coupling. Machines can be interconnected by way of a physical and/or logical network, such as an intranet, the Internet, local area networks, wide area networks, etc. One skilled in the art will appreciate that network communication can utilize various wired and/or wireless short range or long range carriers and protocols, including radio frequency (RF), satellite, microwave, Institute of Electrical and Electronics Engineers (IEEE) 545.11, Bluetooth®, optical, infrared, cable, laser, etc.

Embodiments of the invention can be described by reference to or in conjunction with associated data including functions, procedures, data structures, application programs, etc. which when accessed by a machine results in the machine performing tasks or defining abstract data types or low-level hardware contexts. Associated data can be stored in, for example, the volatile and/or non-volatile memory, e.g., RAM, ROM, etc., or in other storage devices and their associated storage media, including hard-drives, floppy-disks, optical storage, tapes, flash memory, memory sticks, digital video disks, biological storage, etc. Associated data can be delivered over transmission environments, including the physical and/or logical network, in the form of packets, serial data, parallel data, propagated signals, etc., and can be used in a compressed or encrypted format. Associated data can be used in a distributed environment, and stored locally and/or remotely for machine access.

Having described and illustrated the principles of the invention with reference to illustrated embodiments, it will be recognized that the illustrated embodiments can be modified in arrangement and detail without departing from such principles, and can be combined in any desired manner. And although the foregoing discussion has focused on particular embodiments, other configurations are contemplated. In particular, even though expressions such as "according to an embodiment of the invention" or the like are used herein, these phrases are meant to generally reference embodiment possibilities, and are not intended to limit the invention to particular embodiment configurations. As used herein, these terms can reference the same or different embodiments that are combinable into other embodiments.

Embodiments of the invention may include a non-transitory machine-readable medium comprising instructions executable by one or more processors, the instructions comprising instructions to perform the elements of the inventive concepts as described herein.

Consequently, in view of the wide variety of permutations to the embodiments described herein, this detailed description and accompanying material is intended to be illustrative only, and should not be taken as limiting the scope of the invention. What is claimed as the invention, therefore, is all such modifications as may come within the scope and spirit of the following claims and equivalents thereto.

The invention claimed is:

1. A method for securing a membrane material to a gate of a molecular receptor-based chemical field-effect transistor (CHEMFET), the method comprising:
   casting the membrane material onto an exposed region of the gate;
   curing the membrane material;
   placing the CHEMFET into a mold;
   inserting a single application of impervious electrically insulative resin into the mold; and
   securing edges of the membrane material by the single application of the impervious electrically insulative resin, thereby physically preventing lifting off of the membrane material from the gate.

2. The method of claim 1, further comprising preparing the membrane material.

3. The method of claim 2, wherein preparing the membrane material further comprises mixing a rubberized polymer, an ionophore, and a small-molecule receptor.

4. The method of claim 3, wherein:
   the rubberized polymer includes a poly(acrylonitrile-cobutadiene) polymer; and
   the ionophore includes at least one of tetraalkylammonium bromide or tetraalkylammonium nitrate.

5. The method of claim 2, wherein preparing the membrane material further comprises mixing a rubberized polymer, an alkyl-group, and a small-molecule receptor.

6. The method of claim 5, wherein:
   the rubberized polymer includes a poly(acrylonitrile-cobutadiene) polymer; and
   the alkyl-group includes tetradecylammonium bromide.

7. The method of claim 2, wherein preparing the membrane material further comprises mixing a rubberized polymer, a counterion, and a small-molecule receptor.

8. The method of claim 7, wherein:
   the rubberized polymer includes a poly(acrylonitrile-cobutadiene) polymer; and
   the counterion includes at least one of tetraoctylammonium chloride or tetraoctylammonium nitrate.

9. The method of claim 2, wherein preparing the membrane material further comprises mixing 8% to 99% by weight, or thereabout, of poly(acrylonitrile-cobutadiene) polymer, 0.1% to 19% by weight, or thereabout, of tetraoctylammonium bromide, and 0.1% to 10% by weight, or thereabout, of molecular receptor in tetrahydrofuran.

10. The method of claim 1, further comprising removing the CHEMFET from the mold.

11. A method for securing a membrane material to a gate of a molecular receptor-based chemical field-effect transistor (CHEMFET), the method comprising:
   covering an exposed region of the gate of the CHEMFET with a mask;
   encapsulating the CHEMFET by a first application of impervious electrically insulative resin to cover at least a source line and a drain line of the CHEMFET;
   removing the mask, thereby revealing the exposed region of the gate;
   casting the membrane material onto the exposed region of the gate and onto at least some of the first application of the impervious electrically insulative resin;
   curing the membrane material; and
   securing edges of the membrane material by a second application of the impervious electrically insulative resin, thereby physically preventing lifting off of the membrane material from the gate.

12. The method of claim 11, further comprising preparing the membrane material.

13. The method of claim 12, wherein preparing the membrane material further comprises mixing a rubberized polymer, an ionophore, and a small-molecule receptor.

14. The method of claim 13, wherein:
   the rubberized polymer includes a poly(acrylonitrile-cobutadiene) polymer; and
   the ionophore includes at least one of tetraalkylammonium bromide or tetraalkylammonium nitrate.

15. The method of claim 12, wherein preparing the membrane material further comprises mixing a rubberized polymer, an alkyl-group, and a small-molecule receptor.

16. The method of claim 15, wherein:
the rubberized polymer includes a poly(acrylonitrile-cobutadiene) polymer; and
the alkyl-group includes tetradecylammonium bromide.

17. The method of claim 12, wherein preparing the membrane material further comprises mixing a rubberized polymer, a counterion, and a small-molecule receptor.

18. The method of claim 17, wherein:
the rubberized polymer includes a poly(acrylonitrile-cobutadiene) polymer; and
the counterion includes at least one of tetraoctylammonium chloride or tetraoctylammonium nitrate.

19. A sensor module, comprising:
a molecular receptor-based chemical field-effect transistor (CHEMFET), comprising:
  a printed circuit board;
  a substrate coupled to a surface of the printed circuit board;
  a source line coupled to a first bonding pad on the substrate;
  a drain line coupled to a second bonding pad on the substrate;
  a first via formed in the first bonding pad and through the substrate;
  a second via formed in the second bonding pad and through the substrate;
  a gate disposed on the substrate adjacent to an end of the source line and an end of the drain line, and configured to cause an inversion layer to be formed between the ends of the source line and the drain line;
  a membrane material disposed on an exposed gate region of the gate; and
  impervious electrically insulative resin encapsulating the CHEMFET except for the exposed gate region of the gate, the insulative resin disposed on edges of the membrane material and securing the edges of the insulative resin to the gate; and
an amplifier circuit, comprising:
  a source terminal coupled to the source line of the CHEMFET via the first bonding pad and the first via;
  a drain terminal coupled to the drain line of the CHEMFET via the second bonding pad and the second via;
  a gate terminal coupled to the gate of the CHEMFET;
  a reference ground terminal;
  a floating ground terminal;
  a power supply terminal;
  a first differential operational amplifier coupled to the drain terminal, the power supply terminal, the floating ground terminal, and the reference ground terminal;
  a second differential operational amplifier coupled to the source terminal, the gate terminal, the power supply terminal, and the floating ground terminal;
  a third differential operational amplifier coupled to the gate terminal, the power supply terminal, and the floating ground terminal; and
  an output terminal coupled to the third differential operational amplifier, the output terminal being configured to generate an output voltage as an indicator of the quantity of nitrate levels in field ground soil.

20. The sensor module of claim 19, further comprising:
one or more sensor pins coupled to the reference ground terminal, the one or more sensor pins being configured to contact the field ground soil;
a data logger including a memory device configured to store field ground soil nitrate level information over a period of time; and
a transceiver configured to wirelessly transmit the field ground soil nitrate level information to a host probe device that is separate from and external to the sensor module.

* * * * *